United States Patent
Connolly et al.

(10) Patent No.: US 9,816,150 B2
(45) Date of Patent: Nov. 14, 2017

(54) METHOD FOR SELECTION OF AGENTS INFLUENCING INTESTINAL MOTILITY DISORDERS AND PAIN

(71) Applicant: BioGaia AB, Stockholm (SE)

(72) Inventors: Eamonn Connolly, Lidingo (SE); Wolfgang Kunze, Hamilton (CA); John Bienenstock, Toronto (CA)

(73) Assignee: BioGaia AB, Stockholm (SE)

( * ) Notice: Subject to any disclaimer, the term of this patent is extended or adjusted under 35 U.S.C. 154(b) by 0 days.

(21) Appl. No.: 15/389,577

(22) Filed: Dec. 23, 2016

(65) Prior Publication Data

US 2017/0114422 A1    Apr. 27, 2017

Related U.S. Application Data

(62) Division of application No. 14/425,470, filed as application No. PCT/EP2013/068202 on Sep. 3, 2013, now Pat. No. 9,555,065.

(60) Provisional application No. 61/696,277, filed on Sep. 3, 2012.

(51) Int. Cl.
*C12R 1/225* (2006.01)
*A23L 33/135* (2016.01)
*A61K 35/747* (2015.01)

(52) U.S. Cl.
CPC ............ *C12R 1/225* (2013.01); *A23L 33/135* (2016.08); *A61K 35/747* (2013.01); *A23V 2002/00* (2013.01)

(58) Field of Classification Search
None
See application file for complete search history.

(56) References Cited

PUBLICATIONS

Perez-Burgos et al., "Psychoactive bacteria *Lactobacillus rhamnosus* (JB-1) elicits rapid frequency facilitation in vagal afferents", *Am J Physiol Gastrointest Liver Physiol*, (2013) 10 pages.
Lammers et al. "Simulation and analysis of spatio-temporal maps of gastrointestinal motility". *BioMedical Engineering OnLine*, 2008, vol. 7(2), pp. 1-11.
Wang et al. "Lactobacillus reuteri ingestion and IK Ca channel blockade have similar effects on rat colon motility and myenteric neurons", *Neurogastroenterology & Motility*, 2010, 98-e33.
Wang et al. "Luminal administration ex vivo of a live Lactobacillus species moderates mouse jejunal motility within minutes", *The FASEB Journal*, 2010, vol. 24(10), pp. 4078-4088.
Wu et al. "Spatiotemporal Maps of Ex Vivo Peristalsis Reveal Details of Probiotic Effects on Mouse Jejunum Motility", *Canadian Journal of Gastroenterology*, Feb. 27, 2012, pp. 526; A291 (Abstract only).
Wu et al. "Spatiotemporal maps reveal regional differences in the effects on gut motility for Lactobacillus reuteri and rhamnosus strains", *Neurogastroenterology & Motility*, 2013, pp. 1.
International Search Report corresponding to International application No. PCT/EP2013/068202; dated Jan. 22, 2014, 5 pages.

*Primary Examiner* — Oluwatosin Ogunbiyi
(74) *Attorney, Agent, or Firm* — Myers Bigel, P.A.

(57) ABSTRACT

A method is provided for evaluating agents for the treatment of different intestinal motility disorders, using distinct methodological parts related to musculature and nerves of the GI tract which communicate with the brain. In particular, the present invention provides a method for the selection of an agent effective for the treatment of an intestinal motility disorder, comprising: a) a step of spatiotemporal (ST) mapping carried out on a gastrointestinal segment to analyze the effect of the agent on gastrointestinal motility; and b) a step of ex vivo nerve bundle recording carried out on a gastrointestinal segment to analyze the effect of the agent on mesenteric afferent nerve firing. Bacterial strains selected by the methods of the invention and the use of the bacterial strains in the treatment of intestinal motility disorders are also provided.

14 Claims, 9 Drawing Sheets

A. Organ Bath Setup

B. Image Acquisition

C. Conversion to B&W for edge detection

D. Generation of Spatiotemporal Map

METHOD FOR SELECTION OF AGENTS INFLUENCING INTESTINAL MOTILITY DISORDERS AND PAIN

STATEMENT OF PRIORITY

This application is a divisional application of U.S. application Ser. No. 14/425,470, filed Mar. 3, 2015, allowed, which is 35 U.S.C. §371 national phase application of International Application Serial No. PCT/EP2013/068202, filed Sep. 3, 2013, which claims the benefit of U.S. Provisional Patent Application No. 61/696,277; filed Sep. 3, 2012, the entire contents of each of which is incorporated by reference herein.

BACKGROUND OF THE INVENTION

Field of the Invention

The term intestinal motility disorders applies to abnormal intestinal contractions often associated with pain, constipation or diarrhea. This phrase is used to describe a variety of disorders in which the gut has not developed properly or lost its ability to coordinate muscular activity due to various causes. Such disorders may manifest in a variety of ways, and includes but are not limited to the following:
Abdominal distention
Recurrent obstruction
Abdominal colicky pain
Constipation
Gastroesophageal reflux disease
Intractable, recurrent vomiting
Diarrhea
Irritable bowel syndrome (IBS)
Inflammatory bowel disease
Fecal incontinence
Infantile colic
Frequent recurrent abdominal pain (FRAP)
Regurgitation
Food intolerance In a broad sense, any significant alteration in the transit of foods and secretions into the digestive tract may be considered an intestinal motility disorder.

Proper coordinated movements of the stomach and intestines are required to digest and propel intestinal contents along the digestive tract. The patterns of contraction and relaxation necessary for proper motility of the gastrointestinal (GI) tract are complex and uses the nerves and muscles within the GI walls. Every day, at any time, many factors can influence GI motility (e.g., physical exercise, emotional distress). Newborn infants have to develop the complex system of motility in the GI tract. The pathogenesis of intestinal motility disorders is in most cases multifactorial.

Although the overall structural organization of nerves and musculature is similar throughout the small and large intestine, each part has distinct motor activities. Stationary or short propagated contractions with occasional longer peristaltic and antiperistaltic complexes occur during and after feeding and this allows the food bolus to be broken up and mixed with digestive juices for proper absorption. After digestion the motor program changes to one with longer propagated contractions that move digested products in the anal direction. Other motor activity occurs, which is more regular, making the peristaltic waves (i.e., contractions of the circular musculature of the small intestine) that allow progression of undigested food through the intestines.

Aging, dementia, stroke, Parkinson disease, spinal cord injuries, rectal tears during birthing, diabetes, surgical complications, and neuromuscular disorders (e.g., myasthenia gravis) may cause motility disorders.

IBS, a commonly diagnosed disorder of intestinal motility, has been considered a disease of the colon for decades, but research on GI motility has demonstrated that underlying motility disturbances can occur also in the small bowel. IBS may be accompanied by abdominal pain.

The causes of irritable bowel syndrome (IBS) remain unknown. According to some reports, the small intestine and colon of patients with IBS are more sensitive and reactive to mild stimuli than usual.

Occasionally, fecal incontinence may occur after ingestion of certain foods. Sugars, insoluble fibers, and starches (except rice) are normally broken down in the intestines, forming a variable amount of gas that must be expelled. Most people who have lactase deficiency cannot digest lactose, a sugar common in several foods (e.g., milk, cakes). People who have lactose deficiency may experience uncontrolled liquid diarrhea after lactose ingestion.

Constipation is the most common digestive complaint in the United States but despite its frequency, often remains unrecognized until the patient develops secondary disorders, such as anorectal disorders or diverticular disease.

There is no widely accepted clinically useful definition of constipation. Health care providers usually use the frequency of bowel movements (i.e., less than 3 bowel movements per week) to define constipation. However, the Rome criteria, initially introduced in 1988 and subsequently modified twice to yield the Rome III criteria, have become the research-standard definition of constipation.

According to the Rome III criteria for constipation, a patient must have experienced at least 2 of the following symptoms over the preceding 3 months:
Fewer than 3 bowel movements per week
Straining
Lumpy or hard stools
Sensation of anorectal obstruction
Sensation of incomplete defecation
Manual maneuvering required to defecate Constipation is frequently chronic, can significantly affect an individual's quality of life, and may be associated with significant health care costs. It is considered chronic if it occurred for at least 12 weeks (in total, not necessarily consecutively) during the previous year.

Constipation commonly has several causes, either primary or secondary. The most frequent of these are the following:
Diet that is very poor in fiber
Pregnancy
Psychological constipation and clinical depression related to lifestyle changes (e.g., travel, a new job, or divorce), in which the patient ignores the urge to defecate
Hypothyroidism
Electrolyte imbalance, especially if it involves $Ca^{++}$ or $K^+$
Tumors producing mechanical compression on an intestinal tract, either internally or externally
Nervous system injuries
Aging
Parkinson's disease
Intoxication from lead, mercury, phosphorus, or arsenic Constipation is quite common during pregnancy. The muscle contractions that normally move food through the intestines slow down because of higher levels of the hormone progesterone and possibly extra iron taken as prenatal vitamin. This is sometimes also accompanied by lower abdominal pain.

Constipation is also associated with increased age and the so called "the aging gut" commonly found especially in people over 70 and in chronic care institutions. This condition is accompanied by:
Reduced number of neurons in the myenteric plexus impaired response to direct stimulation leading to myenteric dysfunction
Increased collagen deposition of the left colon, leading to abnormalities in colonic and rectal compliance and dysmotility
Reduction in the amplitude of inhibitory nerve input to the circular muscle layer of the colon, resulting in lack of segmental motor coordination
Increased binding of plasma endorphins to intestinal receptors in persons 60 and older At the other end of the aging spectrum intestinal motility disorders, persistent or excessive crying from infant colic is one of the most distressing problems of infancy. It is distressing for the infant, the parents, and the involved healthcare professionals. The parents of the irritable infant may view the crying as an indictment of their caregiving ability or as evidence of illness in their child. Infantile colic is a condition that resolves with time.

The most widely accepted definition for colic is the Wessel criteria or the "rule of three": crying that lasts for more than three hours per day, occurs on more than three days per week, and persists for more than three weeks. This definition also requires that the infant is "otherwise healthy and well fed".

Intestinal hypermotility secondary to a presumed autonomic imbalance also has been proposed as one etiology for colic. Many of the mechanisms that regulate motor activity are immature in infants. The immaturity of these mechanisms may result in increased vulnerability to feeding intolerance. Thus, colic may be a common clinical manifestation in the subpopulation of infants who have maturational dysfunction in one or more of the aspects of motility regulation.

According to some epidemiologic reports, as many as 30 million Americans have intestinal motility disorders. Available data from the medical literature indicate that worldwide, 30-45% of all GI conditions are referable to intestinal motility disorders.

Present treatments and recommendations vary depending on the type of motility disorders, for constipation some examples are:
Fiber or bulking agents (not useful for slow transit constipation)
Stool softeners
Stimulant laxatives
Osmotic laxatives (for example polyethylene glycol)
Chloride-channel activator (for example Lubiproston)
Serotonergic agents (5-HT4 receptor agonists)

Further the use of Lactic Acid Bacteria (LAB) has been studied in a randomized clinical trial: Efficacy of *Lactobacillus paracasei*-enriched Artichokes in the Treatment of Patients With Functional Constipation (Riezzo et al; Aliment Pharmacol Ther. 2012 February; 35(4):441-50)

Also, 90 breastfed colicky infants were randomly assigned to treatment with *L. reuteri* or simethicone in a trial. At baseline, median daily crying time was 197 minutes in both groups. Among the 83 infants who completed the trial, median daily crying time was lower in the *L. reuteri* than in the simethicone group on day 7 (159 versus 177 minutes) and day 28 (51 versus 145 minutes). (Savino F et al, Pediatrics. 2007; 119(1):e124).

Intestinal motility disorders applies to abnormal intestinal contractions often associated with pain, there are many different kinds of treatments and recommendations for the different disorders, some which work better than many others.

So there is an overall need and specific problems to solve for various motility disorders namely; How to best select agents to normalize or treat intestinal motility disorders and gut/intestinal pain?

SUMMARY OF THE INVENTION

The inventors of the invention herein have developed a new method for evaluating agents for the treatment of different intestinal motility disorders, using distinct methodological parts related to musculature and nerves of the GI tract and their communication with the brain.

Thus, the present invention relates to a method for the selection of an agent effective for the treatment of an intestinal motility disorder, wherein said method comprises:
a) a step of spatiotemporal (ST) mapping carried out on a gastrointestinal segment to analyse the effect of an agent on gastrointestinal motility; and
b) a step of ex vivo nerve bundle recording carried out on a gastrointestinal segment to analyse the effect of an agent on mesenteric afferent nerve firing.

In preferred embodiments the ST mapping in step a) is carried out by video imaging or recording. In the methods of the invention, step a) preferably comprises using the ST map generated in step a) to measure migrating motor complex (MMC) frequency and/or migrating motor complex (MMC) velocity in said gastrointestinal segment.

In the methods of the invention, step a) preferably further comprises the measurement of intraluminal pressure, for example intraluminal peak pressure (PPr).

In the methods of the invention, preferably step b) comprises measuring the spontaneous firing frequencies of mesenteric afferent nerve bundles.

In preferred aspects, the present invention discloses a two-step method for selection of agents effective in motility disorders. In the first step the inventors combined intraluminal pressure recordings with spatiotemporal maps to analyze effects of different agents on motility. In this step intraluminal peak pressure (PPr) is preferably measured and video recordings made of mouse ex vivo jejunum and colon segments before and after intraluminal applications of agents. Migrating motor complex frequency and velocity are also calculated in the first step of the method. In the second step intestinal nerve signaling is analyzed and the spontaneous firing frequencies of mesenteric afferent nerve bundles is measured. Thus, the present invention discloses a method for selection of agents effective in motility disorders comprising a first step using simultaneous recording of intraluminal pressure changes in addition to video recording and spatiotemporal maps and a second step which is an analysis of nerve signaling, for example by taking mesenteric, e.g. extracellular mesenteric, nerve recordings.

Thus, in a yet further embodiment, the present invention provides a method for the selection of an agent effective for the treatment of an intestinal motility disorder, comprising the steps:
(a) recording intraluminal pressure, creating a spatiotemporal (ST) map to enable an analysis of the effects of different agents on gastrointestinal motility wherein said spatiotemporal map is used to measure migrating motor complex frequency and velocity, in an intestinal sample in the presence and absence of a test agent; and (b) analysing intestinal nerve signalling by measuring the spontaneous firing frequencies of mesenteric afferent nerve bundles in an intestinal sample in the presence and absence of a test agent.

In preferred embodiments of this method in step (a) intraluminal peak pressure (PPr) is measured.

The present invention relates to the described two-step method and also to new bacterial strains.

DETAILED DESCRIPTION OF THE INVENTION AND PREFERRED EMBODIMENTS THEREOF

Figure 1:
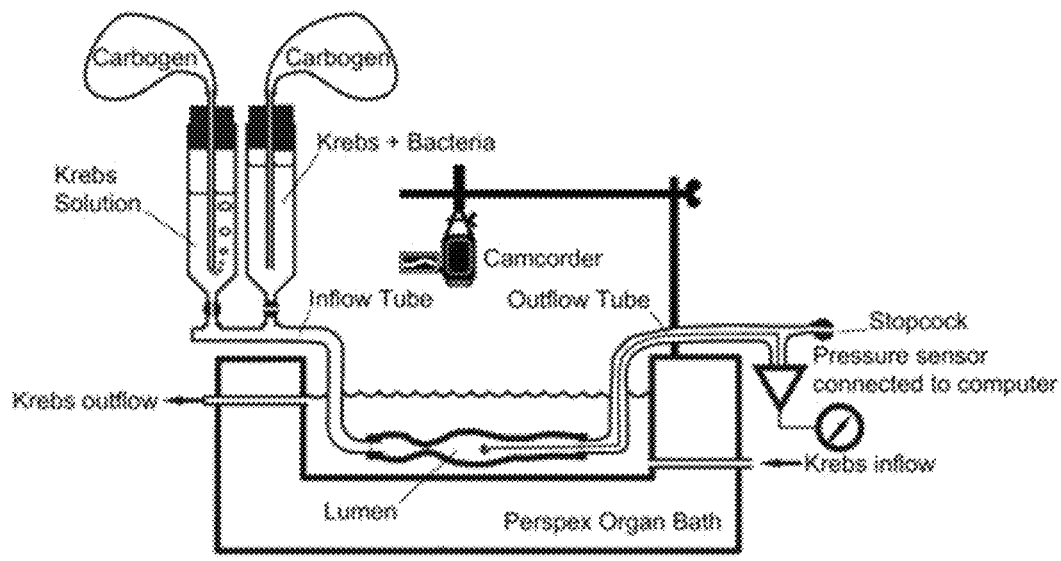
FIG. 1 Organ motility recordings
Figure 1:
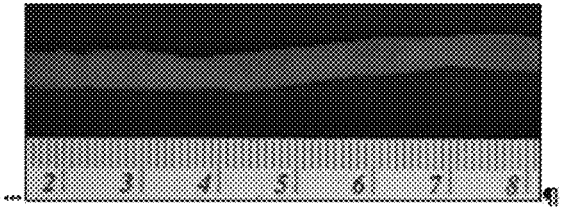
Figure 1:
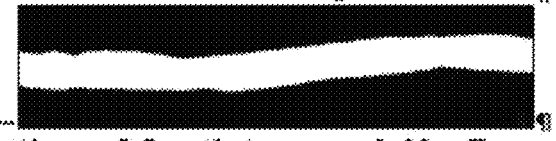
Figure 1:
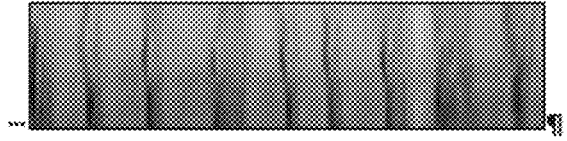

To facilitate understanding of the invention, a number of terms are defined below.

As used herein the term "intraluminal peak pressure" (PPr) is based on intraluminal pressure recordings, where intraluminal pressure changes are measured at the midpoint of the longitudinal axis of the gut segment. The pressure signal is analyzed and intraluminal peak pressure (PPr) is identified and measured.

As used herein the term "migrating motor complex frequency" (MMC frequency) is calculated by counting the number of dark MC bands in the spatiotemporal maps.

As used herein the term "migrating motor complex velocity" (MMC velocity) is measured from the slope(s) of each band in the spatiotemporal map generated by migrating motor complexes.

As used herein the term "firing frequency" is used to measure the sensory spike trains to the brain.

As used herein the term "agent" is used to mean any substance or material including whole cells, microorganisms, proteins, peptides, enzymes, molecules or other biological or chemical material that can be used to influence motility and or pain in the gastro intestinal system of a mammal. Preferred agents are bacterial strains, e.g. probiotic bacterial strains.

The method of the invention herein is a two step method, based on a spatiotemporal (ST) mapping method (step 1) combined with an improved technology for nerve bundle recording ex vivo (step 2) in which a gastro intestinal segment is excised with or without the mesenteric arcade containing the nerve bundle supplying the segment made up of both spinal and vagal fibers.

In the first step of the presented preferred method intraluminal pressure recordings are combined with spatiotemporal (ST) maps to analyze the effects of different agents on motility.

ST maps provide a tool for visualizing a temporally evolving and spatially varying field, which can be used in the analysis of gastrointestinal motility including behaviors in health and motility disorders. Using spatiotemporal video imaging the inventors herein have developed a part of the new method using computer analysis of spatiotemporal maps of changes in gut diameter. This reveals motor patterns that are very difficult to detect with any other technique. The parameters of these patterns directly correlate results obtained with mouse ex vivo intestinal segments with human gut pharmacology. The peristaltic propagated motor complexes (MCs) or mixing movements (stationary MCs) are digitally recorded in real-time and the images stored. The analysis software, as described further down, detects the edges of the intestine and is able to automatically calculate the diameter along the length of the segment over time. This data is used by the program to construct spatiotemporal maps that are able to extract highly specific information about motor patterns; for example, migrating motor complex (MMC) frequency (neurally dependent MMC frequency), MMC velocity and myogenic (slow wave related) contraction rates of contraction.

Further, it is beginning to be accepted that intestinal microorganisms signal to the brain as part of the so called microbiome-gut-brain axis. However, very little is known about the role of the gut microbiome in the development or function of the nervous system. Nothing is presently known about the quantitative nature of the nervous signal relayed from gut to the central nervous system.

Single sensory neurons, including those among the vagus fibers, represent continuous physical stimuli as patterned spike trains that encode the nature and intensity of the stimulus. In addition to this, stimuli may be represented in a population code determined by the number of active fibres in the bundle. All the information reaching the brain via primary afferents has to be encoded in the language of neuronal spike trains. Therefore, knowing how the sensory spike trains are affected by commensals, probiotic strains and different substances enable us to identify new beneficial gut microorganisms and their active molecules by their effects on primary afferent firing as well as new drugs and other compounds that in various fashion can intervene in this signaling system.

The new method of the invention herein for evaluating agents for the treatment of different intestinal motility disorders allows differentiation of specific effects of the agents, for example a probiotic bacterial strain or another biological or chemical agent, on both muscle and on nerves. Experimental data confirms that it is not necessarily the same agent that is able to modulate for example mixing pattern or propulsion pattern in a certain part of the GI tract that also is the most effective in modulating pain associated with enteric and/or the central nervous system.

Furthermore, to investigate the effects of certain molecules in different diseases, our method allows different studies of luminal perfusion and diffusion to and across the epithelial barrier.

Two fundamental patterns of motility are conducted by the digestive tube:

Propulsion: foods must be propelled along the full length of the digestive tube in order to be subjected to the sequential series of processing involved in disassembly and absorption. The principal type of propulsive motility, seen particularly in the esophagus and small intestine, is peristalsis—a ring of muscle contraction moves from the oral side of a bolus of ingesta and toward the anus, propelling the contents of the lumen in that direction; as the ring moves, the muscle on the other side of the distended area relaxes, facilitating smooth passage of the bolus.

Mixing: If ingested materials were simply propelled through the digestive tube, you would expect very poor digestion and absorption, because the digestive enzymes would not be adequately mixed with the ingesta and the bulk of the ingesta would not come in contact with the epithelial cells that absorb nutrients, including water. Segmentation contractions are a common type of mixing motility seen especially in the small intestine—segmental rings of contraction chop and mix the ingesta. Alternating contraction and relaxation of the longitudinal muscle in the wall of the gut also provides effective mixing of its contents.

Using the new method herein, changed gut motility, seen as either the mixing pattern (post feeding) or the propulsive pattern, seen clearly using the ST-map method, in combination with changes in pain caused by different motility disorders, and manifested centrally or peripherally, can be detected and recorded.

One kind of pain is visceral pain that results from the activation of nociceptors of the abdominal viscera (organs). Visceral structures are highly sensitive to distension (stretch), ischemia and inflammation, but relatively insensitive to other stimuli that normally evoke pain. Visceral pain is diffuse, difficult to localize and often referred to a distant, usually superficial, structure. It may be accompanied by symptoms such as nausea, vomiting, changes in vital signs as well as emotional manifestations. The pain may be described as sickening, deep, squeezing, and dull. Distinct structural lesions or biochemical abnormalities explain this type of pain in only a proportion of patients. These diseases are sometimes grouped under gastrointestinal neuromuscular diseases (GINMD). Persons can also experience visceral pains, often very intense in nature, without any evidence of structural, biochemical or histolopathologic reason for such symptoms.

A nociceptor is a sensory receptor that responds to potentially damaging stimuli by sending action potentials to specific nociceptive neurons (Aδ or C) which transmit to the anterolateral tracts of the spinal cord (plus a minor vagal projection) and then to the thalamus, and prosencephalon including the insular and cingulate cortices. Critical for pain perception originating in the gut pathology is the activation of pain messages from the gut to the central nervous system via extrinsic primary afferent fibres that travel in mesenteric afferent nerve bundles.

In the system of the invention herein, changes in motility and pain, are read outs as alterations in motility patterns (for example PPr, MMC velocity and/or MMC frequency) or contraction amplitudes or increased afferent mesenteric nerve spinal traffic for specific and selected parts of the gut. It has been surprising to find that different agents can promote mixing in one part of the GI tract and propulsion in another part, or have no effect at all, and influence pain signaling systems in one part, but not in another part of the GI-tract, and via different nerve pathways such as vagal or for visceral pain through the dorsal root ganglion. Such precise regional specificity highlights the power and specificity of our approach in assessing the effects of test molecules.

It is therefore an object of the present invention to find agents suitable for treatment, prevention or modulating specific motility disorders, by using the model herein.

The two steps in the method presented will provide data on gastrointestinal motility and mesenteric afferent nerve firing. Analyzing these parameters will result in a method of selecting for agents effective in the treatment of an intestinal motility disorder. Thus, the analysis of the effect of an agent in step a) and step b) of the provided methods is used to determine whether the agent is effective for the treatment of an intestinal motility disorder.

Preferred parameters to be measured in step a) are MMC frequency and/or MMC velocity and this is conveniently done by way of an STmap which is preferably generated by video imaging, e.g. using a video recording, and preferably comprises a pattern of alternating bands of light and dark hues that contains 3 sets of information: position along the gut (ordinate), time (abscissa) and gut diameter (applicate or z-axis). Using these variables, the spatiotemporal map can become a motility "fingerprint" whose sensitivity is important in defining the detailed and nuanced effects that specific probiotic strains and other agents have on motility and the ability to distinguish between them.

Other preferred parameters to be measured in step a) are intraluminal pressure, in particular intraluminal peak pressure (PPr). Other parameters, for example as described in the Examples, can optionally be measured from the ST map and in step a) of the method.

A preferred parameter to be measured in step b) is the spontaneous firing frequencies of mesenteric afferent nerve bundles. This technique can be used to determine changes in the excitability of the mesenteric nerve fibres induced by different treatments.

Analyzing one or more of these parameters will result in a method of selecting agents effective in motility disorders. Appropriate methods and apparatus for generating the ST map and measuring these parameters are described in the experimental Examples and Figures.

Thus, in preferred methods, the two steps in the method presented will give data on intraluminal peak pressure (PPr), MMC frequency, MMC velocity and spontaneous firing frequencies of mesenteric afferent nerve bundles. Analyzing all of these parameters will result in a preferred method of selecting agents effective in motility disorders.

The methods of the invention may be used to find suitable agents for different motility disorders. Agents are chosen to affect the MMC velocity and/or MMC frequency and/or PPr and nerve firing frequency of the patient in a beneficial way in order to influence, prevent or treat the motility disorder.

Step a) of the method uses ST mapping (ST analysis) of a gastrointestinal segment to analyse the effect of an agent on gastrointestinal motility. To do this preferably the MMC frequency and/or MMC velocity are measured using the ST map. Conveniently the ST map shows images of MC bands from which the frequency and velocity can be measured, for example as described in the experimental Examples. In addition, preferably the intraluminal pressure and, more preferably, the intraluminal peak pressure (PPr) is measured within the gastrointestinal segment.

The gastrointestinal segment for use in the methods of the present invention can be from any appropriate part of the gastrointestinal tract, for example can be a segment from the small intestine (e.g. jejunum) or from the large intestine (e.g. colon). Appropriate segments for step b) of the method will require the presence of an appropriate nerve bundle to enable the measurement of mesenteric afferent nerve firing. This can conveniently be provided by having a gastrointestinal segment with attached mesenteric tissue, for example as described in the experimental Examples. Thus, the methods of the invention are conveniently carried out on ex vivo segments from an appropriate experimental animal, for example on mouse gastrointestinal segments (e.g. mouse colon or jejunum segments). Surprisingly, the methods of the present invention can detect differences in the action of the same agent on both types of intestinal section. The ability to carry out a comparison of the effect of an agent on the small versus the large intestine could be advantageous, particularly as, depending on the intestinal motility disorder to be treated and the clinical stage and symptoms thereof, a treatment which is region-specific, e.g. specific for either the small or large intestine might be beneficial.

Changes in gastrointestinal motility induced by an agent can be detected as a read out in step a) of the method, for example as an alteration in motility pattern or contraction amplitudes. Some agents will have no effect at all. An agent which can increase gastrointestinal motility, for example by increasing the MMC frequency and/or MMC velocity and/or intraluminal pressure such as PPr will likely be useful to treat disorders in which it would be advantageous to increase the propulsive motility along the digestive tube such as constipation and colic. If an agent is shown to reduce or not significantly change gastrointestinal motility, for example by reducing or not significantly changing the MMC frequency and/or MMC velocity and/or intraluminal pressure such as PPr, then such an agent would be unlikely to be useful to treat such disorders and would not be selected, particularly if there is a reduction or no significant change in all the parameters measured. However, an agent which can result in a reduction in gastrointestinal motility, for example by reducing one or more of MMC frequency and/or MMC velocity and/or intraluminal pressure such as PPr will likely be useful to treat disorders in which it would be advantageous to decrease the propulsive motility along the digestive tube, such as IBS or diarrhea.

An increase in gastrointestinal motility, for example an increase in the MMC frequency and/or MMC velocity and/or intraluminal pressure such as PPr in a segment of large intestine, by an agent in the methods of the invention is particularly preferred to select an agent for use to treat constipation or colic.

Step b) of the methods of the invention analyses the effect of an agent on mesenteric afferent nerve firing (pain signaling) and can thus be used as a read out for pain, i.e. whether or not an agent is likely to have an effect on pain, e.g. visceral pain. An increase or no significant effect on afferent nerve firing is indicative of an agent which is likely to result in an increase in pain, or no significant effect on pain, respectively, whereas a decrease in afferent nerve firing is indicative of an agent which will reduce pain. Preferred agents are thus those that result in a decrease in afferent nerve firing, e.g. a decrease in the spontaneous firing frequency of afferent nerve bundles. Alternatively, an agent which results in no significant change in nerve firing might be selected if the strain shows advantageous properties as measured by step a) of the method.

The agent to be tested is added to the chosen gastrointestinal segment in any appropriate manner. Conveniently, the agents are added to the intraluminal space of the segment, i.e. are applied intraluminally. In order to analyse the effect of the agent on motility (in step a) or pain signalling (in step b), the steps are conveniently carried out in the presence and the absence of the agent. For example, steps a) and b) are carried out before and after the agent is applied. Thus, in such methods the effect of the agent is compared to an appropriate control, for example the results in the presence of the test agent are compared with the results in the absence of a test agent, e.g. results with buffer alone as opposed to buffer plus agent (e.g. buffer plus a bacterial strain).

Thus, a yet further aspect of the invention provides an agent selected by the methods of the invention. A preferred agent is a microorganism, more preferably a bacterial strain, preferably a probiotic bacterial strain. The agents selected by the methods of the invention may take the form of a pharmaceutical compound or composition or a nutritional compound or composition.

As described above, depending on the motility disorder which it is desired to be treated, the selection criteria will vary. For example, if the intestinal motility disorder is one in which it is desired to reduce the transit time of material through the intestine (or to increase the propulsive motility along the digestive tube), e.g. constipation, regurgitation or colic, then in step a) of the method, an agent of interest will act to increase gastrointestinal motility, for example by increasing MMC frequency or MMC velocity or intraluminal pressure (e.g. PPr). Preferred agents will increase two or more of these parameters, for example will increase MMC frequency and MMC velocity or will increase MMC frequency and intraluminal pressure (e.g. PPr), or will increase MMC velocity and intraluminal pressure (e.g. PPr). Most preferred agents will increase all of these parameters, for example will increase MMC frequency, MMC velocity and intraluminal pressure (e.g. PPr). Step a) of the method can be assessed on an appropriate gastrointestinal segment from the small or large intestine, for example a jejunal segment for the small intestine or a colon segment for the large intestine. In some embodiments, the use of large intestine, e.g. colon segments, is preferred.

For the treatment of such disorders, an agent will be selected which does not effect or does not increase pain signalling, or preferably acts to decrease pain signalling. In step b) of the method such agents will have no effect or will preferably act to reduce or decrease mesenteric afferent nerve firing. Preferably said agent will have no effect on or will preferably act to reduce the spontaneous firing frequencies of mesenteric afferent nerve bundles. Step b) of the method can be assessed on any appropriate gastrointestinal segment from the small or large intestine, for example a jejunum segment for the small intestine or a colon segment for the large intestine. In some embodiments, the use of small intestine, e.g. jejunum segments is preferred.

Using the method of the present invention, the inventors have selected a new bacterial strain, *Lactobacillus gasseri* 345A (LG345A), which has been shown to increase gastrointestinal motility by way of being shown to increase MMC frequency, MMC velocity and intraluminal peak pressure. This strain has also been shown to decrease pain signalling by decreasing mesenteric afferent nerve firing (by decreasing the frequency of firing of mesenteric afferent nerve bundles). This isolated bacterial strain (and other strains, e.g. *L gasseri* strains, with the characteristics, e.g. the ability to induce the above mentioned effects on gastrointestinal motility and pain signalling, of this deposited strain) forms a preferred aspect of the invention and can be used to treat intestinal motility disorders, particularly those in which it is desired to reduce the transit time of material through the intestine. Thus, preferred conditions to be treated with this strain are constipation or colic. Strains, e.g. *L gasseri* strains, which can increase gastrointestinal motility by having the ability to increase each of MMC frequency, MMC velocity and intraluminal peak pressure, and which can decrease pain signalling, e.g. by having an ability to decrease mesenteric afferent nerve firing (e.g. by decreasing the frequency of firing of mesenteric afferent nerve bundles) form preferred aspects of the present invention.

Alternatively, if for example, the intestinal motility disorder for treatment is one in which it is desired to increase the transit time of material through the intestine (e.g. disorders involving rapid passage transit), e.g. IBS or diarrhea, then in step a) of the method, an agent of interest will act to decrease gastrointestinal motility, for example by decreasing MMC frequency or MMC velocity or intraluminal pressure, e.g. PPr. Preferred agents will decrease at least MMC velocity. Preferred agents will decrease two or more of these parameters, for example will decrease MMC velocity and MMC frequency or will decrease MMC frequency and intraluminal pressure (e.g. PPr) or will decrease MMC velocity and intraluminal pressure (e.g. PPr). Most preferred agents will decrease all of these parameters, for example will decrease MMC frequency, MMC velocity and intraluminal pressure (e.g. PPr). Step a) of the method can be assessed on an appropriate gastrointestinal segment from the small or large intestine, for example a jejunal segment for the small intestine or a colon segment for the large intestine. In some embodiments, the use of large intestine, e.g. colon, segments is preferred.

For the treatment of such disorders, an agent will be selected which does not effect or does not increase pain signalling, or preferably acts to decrease pain signalling. In step b) of the method such agents will have no effect or will preferably act to reduce or decrease mesenteric afferent nerve firing. Preferably said agent will have no effect on or will preferably act to reduce the spontaneous firing frequencies of mesenteric afferent nerve bundles. Step b) of the method can be assessed on an appropriate gastrointestinal segment from the small or large intestine, for example a jejunal segment for the small intestine or a colon segment for the large intestine. In some embodiments, the use of small intestine, e.g. jejunum, segments is preferred.

Using the method of the present invention, the inventors have selected a new strain, *Lactobacillus gasseri* 621A (LG621A), which has been shown to decrease gastrointestinal motility by way of being shown to decrease MMC velocity and have no effect on MMC frequency or intraluminal peak pressure. This strain has also been shown to decrease pain signalling by decreasing mesenteric afferent nerve firing (by decreasing the frequency of firing of mesenteric afferent nerve bundles). This isolated bacterial strain (and other strains, e.g. *L gasseri* strains, with the characteristics, e.g. the ability to induce the above mentioned effects on gastrointestinal motility and pain signalling, of this deposited strain) forms a preferred aspect of the invention and can be used to treat intestinal motility disorders, particularly those in which it is desired to increase the transit time of material through the intestine (e.g. disorders involving rapid passage transit). Thus, preferred conditions to be treated with this strain are IBS or diarrhea. Strains, e.g. *L gasseri* strains, which can decrease gastrointestinal motility, e.g. by having the ability to decrease one or more of MMC frequency, MMC velocity and intraluminal peak pressure (preferably MMC velocity), and which can decrease pain signalling, e.g. by having an ability to decrease mesenteric afferent nerve firing (e.g. by decreasing the frequency of firing of mesenteric afferent nerve bundles) form preferred aspects of the present invention.

It is clear from the above that the methods of the invention can also be used to select or identify agents which are not appropriate for the treatment of intestinal motility disorders, for example agents which do not show any effect on one or more, or two or more, or all three of MMC velocity or MMC frequency or intraluminal pressure may not be suitable for use in the treatment of intestinal motility disorders, especially if such agents do not have a beneficial effect on reducing pain signalling. In particular those agents which show no effect on any of these parameters are unlikely to be suitable for the treatment of an intestinal motility disorder. In addition, those agents which have an effect of increasing pain signalling as measured by an increase in mesenteric afferent nerve firing in step b) of the method are unlikely to be suitable for the treatment of an intestinal motility disorder.

Thus, a yet further preferred aspect of the invention provides an agent, preferably a bacterial strain, selected by the method of the invention for use in therapy, more particularly for use in the treatment of an intestinal motility disorder such as those described herein. Appropriate intestinal motility disorders to be treated are described elsewhere herein. Preferred intestinal motility disorders to be treated by the agents or bacterial strains of the invention are those in which it is desired to reduce the transit time of material through the intestine, for example colic, regurgitation or constipation. Other preferred intestinal motility disorders are those in which it is desired to increase the transit time of material through the intestine, for example IBS or diarrhea.

Methods of treatment of a subject with an intestinal motility disorder are also provided by the present invention, said methods comprising the administration of an agent, preferably a bacterial strain, selected by the method of the invention, to said subject in an amount effective to treat said intestinal motility disorder.

Methods of treatment of a subject with an intestinal motility disorder are also provided by the present invention, said methods comprising the administration of a bacterial strain of the invention to said subject in an amount effective to treat said intestinal motility disorder. Preferred strains are LG345A or LG621A for the treatment of intestinal motility disorders as described elsewhere herein.

Preferred intestinal motility disorders and other preferred features are as described elsewhere herein for other aspects of the invention.

Also provided by the present invention is the use of an agent, preferably a bacterial strain, selected by the method of the invention, in the manufacture of a composition or medicament for use in the treatment of an intestinal motility disorder.

Also provided by the present invention is the use of a bacterial strain of the invention, in the manufacture of a composition or medicament for use in the treatment of an intestinal motility disorder. Preferred strains are LG345A or LG621A for the treatment of intestinal motility disorders as described elsewhere herein.

Preferred intestinal motility disorders and other preferred features are as described elsewhere herein for other aspects of the invention.

In the methods and uses of the present invention described herein, the terms "increase", "decrease", "reduce", etc., refer to a measurable change in levels, preferably a significant change in levels, more preferably a statistically significant change, preferably with a probability value of $\leq 0.05$.

Preferred subjects for treatment using the methods of the invention are mammals, more preferably humans. Where the intestinal motility disorder to be treated is constipation then preferred subjects are elderly patients or pregnant women. An elderly patient will generally be understood to be a patient aged 70 or over. Where the intestinal motility disorder to be treated is colic, preferably this is infantile colic.

A yet further aspect of the invention provides a product comprising the agents or strains of the invention (e.g. agents or strains selected by the methods of the invention) for the therapeutic uses as defined elsewhere herein, wherein said use further comprises the administration of at least one further therapeutic or nutritional agent. In such embodiments, the further therapeutic agent can be any further agent which is useful in the treatment of the intestinal motility disorder in question. The further nutritional agent can be any appropriate nutritional component, e.g. a foodstuff or a food supplement.

Said further agents can be administered together with the agent or strain of the invention (e.g. as a composition) or can be administered separately. In addition, said further agents can be administered at the same time as the agent or strain of the invention or at different time points. Suitable administration regimes and timings can readily be determined by the skilled person depending on the further agent in question.

The present invention also provides a composition comprising:
(i) an agent, preferably a bacterial strain, obtainable by the selection method of the invention, or a bacterial strain of the invention as otherwise defined herein; and
(ii) at least one additional component selected from the group consisting of a pharmaceutically acceptable carrier, diluent or excipient, a foodstuff or food supplement, or a further therapeutic or nutritional agent. Thus, said compositions can be formulated as pharmaceutical compositions or as nutritional compositions, e.g. as a food product.

The therapeutic uses of the agents, strains and compositions of the invention as defined herein include the reduction, prevention or alleviation of the relevant disorder or symptoms of disorder (e.g. can result in the modulation of disease symptoms). Such reduction, prevention or alleviation of a disorder or symptoms thereof can be measured by any appropriate assay. Preferably the reduction or alleviation of a disorder or symptoms is statistically significant, preferably with a probability value of <0.05. Such reduction or alleviation of a disorder or symptoms are generally determined compared to an appropriate control individual or population, for example a healthy subject or an untreated or placebo treated subject.

An appropriate mode of administration and formulation of the agents, strains, compositions, etc., is chosen depending on the site of disease. A preferred mode of administration is oral, however, equally for some treatments intravenous or intramuscular injection will be appropriate.

Appropriate doses of the agents, strains and compositions of the invention as defined herein can readily be chosen or determined by a skilled person depending on the disorder to be treated, the mode of administration and the formulation concerned.

As described above, using the invention herein the inventors have obtained two new strains, *Lactobacillus gasseri* 345A and *Lactobacillus gasseri* 621A. These strains have been deposited at DSMZ (Leibniz Institute DSMZ—German Collection of Microorganisms and Cell Cultures, Inhoffenstr. 7B, D-38124 Braunschweig, Germany) on 18 Apr. 2013 and have been designated the numbers DSM 27123 and DSM 27126, respectively.

The discovery by the inventors herein that effects of an agent influencing motility disorders are in most cases multi factorial and are different in various part of the GI-tract and consequently have to be studied in that way to find the best agent for the specific disorder, led to the method of the invention.

It is therefore an object of the present invention to find agents suitable for treatment, prevention or modulating specific motility disorders, by using the model herein.

In one embodiment of the invention the object is to select a compound or other agent, with potential uses as either a nutritional compound or a pharmaceutical, that is effective in preventing or to treat constipation in humans, especially elderly.

In one embodiment of the invention the object is to select a probiotic bacterial strain that can be effective in preventing or treating constipation in humans, especially elderly subjects or pregnant women.

In another embodiment, the object of the invention is to select an agent, for example a probiotic strain, that can be effective in preventing or treating infantile colic.

In another embodiment, the object of the invention is to select an agent, for example a probiotic strain, that can be effective in preventing or treating diarrhea or other motility disorders wherein it is beneficial to decrease velocity and thereby increase transit time.

In one embodiment of the invention the object is to select an agent, for example a probiotic strain, that can be effective in treating or modulating symptoms of Irritable bowel syndrome (IBS). Such an agent is selected to increase transit time, preferably without causing any pain and preferably to reduce pain.

In yet another embodiment, the object of the invention is to select an agent, for example a probiotic strain, that can be effective in preventing fecal incontinence.

In yet another embodiment, the object of the invention is to select an agent, for example a probiotic strain, that can be effective to increase mixing in the small and large intestine without causing any pain and preferably reducing pain, to facilitate or result in better nutritional uptake in a subject, especially in elderly.

The following are some examples of the invention, which are not meant to be limiting of the use of the invention herein but to show practical examples in detail how the invention may be used. Example 1 relates to the description of the spatiotemporal mapping (StMap) software plugin and Example 2 relates to the steps of the selection of effective agents and Example 3 to a selection of agents for a specific motility disorder.

EXAMPLE 1

Description of the StMap Plug-in for the NIH ImageJ Software;

ImageJ is a public domain Java image processing program inspired by NIH Image for the Macintosh. It runs, either as an online applet or as a downloadable application, on any computer with a Java 1.4 or later virtual machine. Downloadable distributions are available for Windows, Mac OS, Mac OS X and Linux.

ImageJ was designed with an open architecture that provides extensibility via Java plugins. Custom acquisition, analysis and processing plugins can be developed using ImageJ's built in editor and Java compiler. User-written plugins make it possible to solve almost any image processing or analysis problem.

Figure 6:
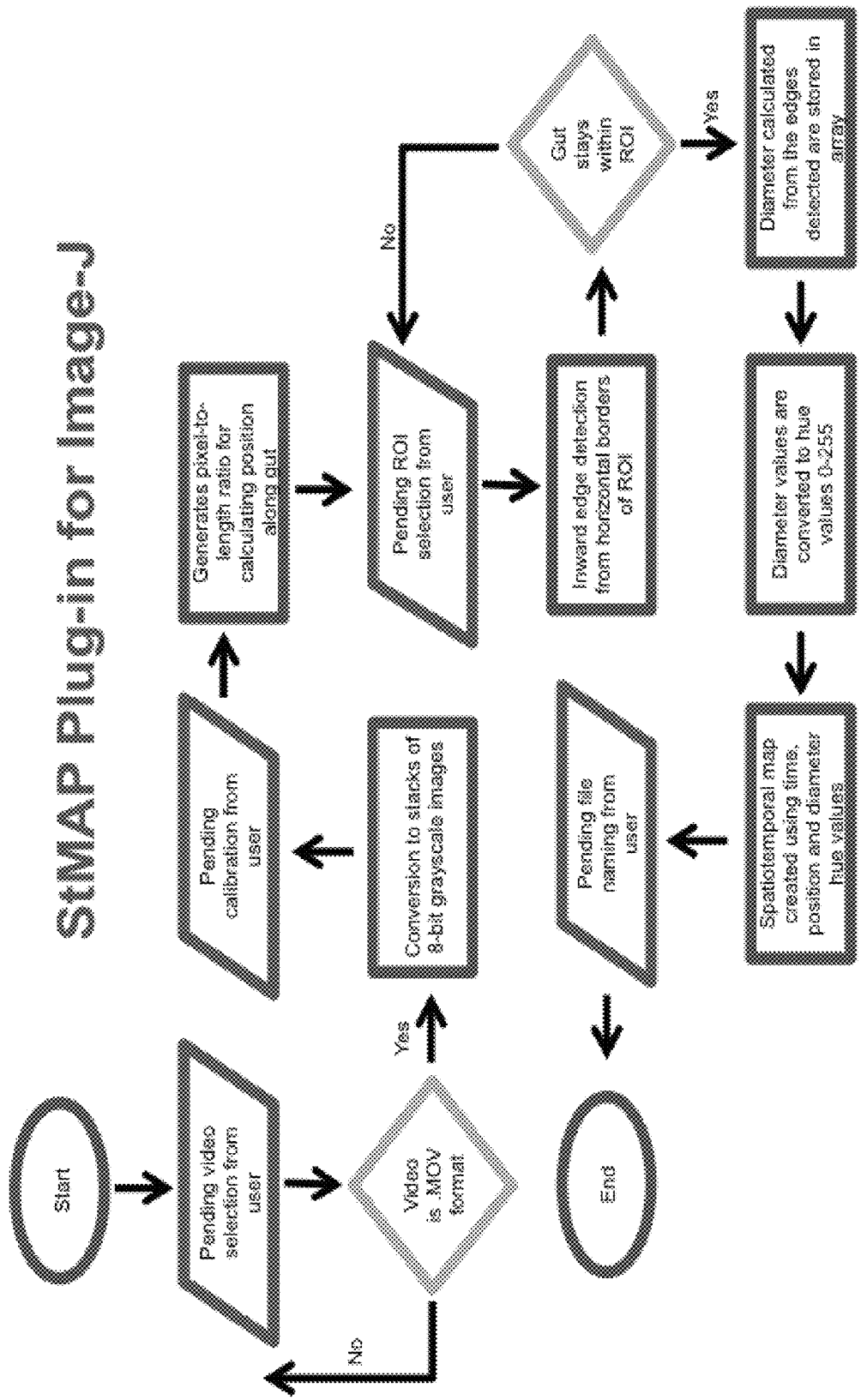
FIG. 6 Details of the StMAP plug-in software

We developed the plug-in following the description of the software available from the National Institutes of Health (NIH), 9000 Rockville Pike, Bethesda, Md., USA) according to the details in FIG. 6.

ROI stands for "Region of Interest"

EXAMPLE 2

Selection of Agents Effective in Motility Disorders.

This selection comprises a two-step method. The first step using simultaneous recording of intraluminal pressure changes in addition to video recording and spatiotemporal maps. The second step is an analysis of nerve signaling.

All agents are compared to a control and the agents are not compared to each other, this will result in one graph per agent tested.

First Step, Spatiotemporal Analysis

We used adult male Swiss Webster mice (20-30 g) bought from Charles River Laboratories (Wilmington, Mass., USA). The mice were killed by cervical dislocation, in line with McMaster guidelines for the use and care of animals. All ensuing procedures were ex vivo.

Organ Bath Motility Recordings 4-cm-long jejunal or distal colon segments were excised and the contents allowed to empty by flushing the segment with Krebs saline under 2 hPa gravity pressure head. Each segment was mounted in a 20-ml organ bath chamber and submerged in oxygenated Krebs (FIG. 1A). Oral and anal ends were cannulated, and the lumen was gravity perfused with (95% $O_2$ and 5% $CO_2$)—gassed Krebs using several Mariotte bottles. The intraluminal compartment was perfused at 0.5 ml/min with room temperature buffer (19 to 22° C.). The organ chamber (serosal compartment) was perfused with pre-warmed (34° C.), carbogen-gassed, Krebs solution at a rate of 5 ml/min). Oxygenated Krebs buffer was of the following composition (mM): 118 NaCl, 4.8 KCl, 25 $NaHCO_3$, 1.0 $NaH_2PO_4$, 1.2 $MgSO_4$, 11.1 glucose, and 2.5 $CaCl_2$ bubbled with carbogen gas (95% Oz and 5% $CO_2$). At the beginning of the experiment, intraluminal pressure was adjusted to 3 hPa and the recordings were made at this filling pressure. Bacteria were applied by switching the oral luminal inflow from Marriotte bottles containing Krebs to ones containing Krebs plus bacteria by closing and opening the appropriate stopcocks, as illustrated in FIG. 1A. Intraluminal pressure changes were measured at the midpoint of the longitudinal axis of the gut segment. The pressure signal was amplified, digitized, stored on a PC computer and analyzed off-line using PClamp 9 software (Molecular Devices, Sunny Vale, Calif., USA).

Images were recorded using a video camcorder (JVC Everio Hard Disk Camcorder Model GZ-MG155U) which was placed 10 cm above a gut segment (FIG. 1A). Recording was started in synchrony with the pressure recording using an 8 to 12 cm field of view for the duration of the experiment. The camera output was in raw video format (MOD) at 30 frames per second (fps). 10-min long video clips were excised from the MOD file using video editing software (Avidemux version 2.5.0, Open source software available from Avidemux). The clips were then converted into the MOV format using a video converter (Zune converter version 1.1, Open source software available at the FFmpeg website). The final video clips were resampled to a resolution of 384×256 pixels and 25 fps.

Video recordings were analyzed using in-house image processing software (StMap, see example 1) developed as a plug-in for NIH ImageJ (version 1.43c, Open source software available from the NIH). The software converts the image (1B) in each frame of the video into a black-and-white silhouette (1C) and generates a spatiotemporal map using an edge detection routine. The routine first measures the diameter at each position along the gut and it then represents the physical diameter at each position as a hue value (ranges from 0-255, black to white). As gut diameter decreases during contractions, the hue value is reduced towards 0 and will be shown as toward darker values. As the software reads through each 10 minute clip, it generates a spatiotemporal map—a pattern of alternating bands of light and dark hues that contains 3 sets of information: position along the gut (ordinate), time (abscissa) and gut diameter (applicate or z-axis) (FIG. 1D). Using these variables, the spatiotemporal map becomes a motility "fingerprint" whose sensitivity is critically important in defining the detailed and nuanced effects that specific probiotic strains and other agents have on motility and the ability to distinguish between them.

Figure 2:
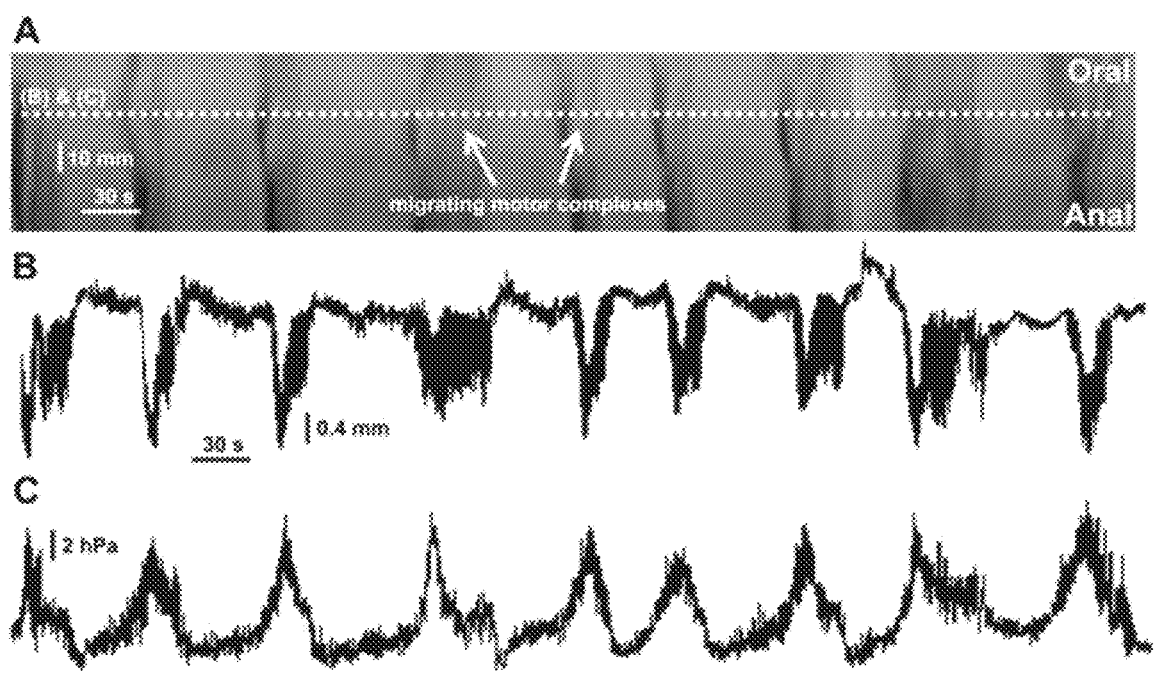
FIG. 2 Picture and data output from motility recordings

Since the StMap measures the diameter changes at each position, StMap can be interpreted as a stacking of numerous 2D diameters versus time graphs. In fact, for map, if the location of the pressure transducer were identified (dotted line in FIG. 2A) and were shown as a grey scale versus time graph (FIG. 2B), this graph would be in register with the simultaneously recorded pressure vs. time recording at that locus (FIG. 2C).

Figure 3:
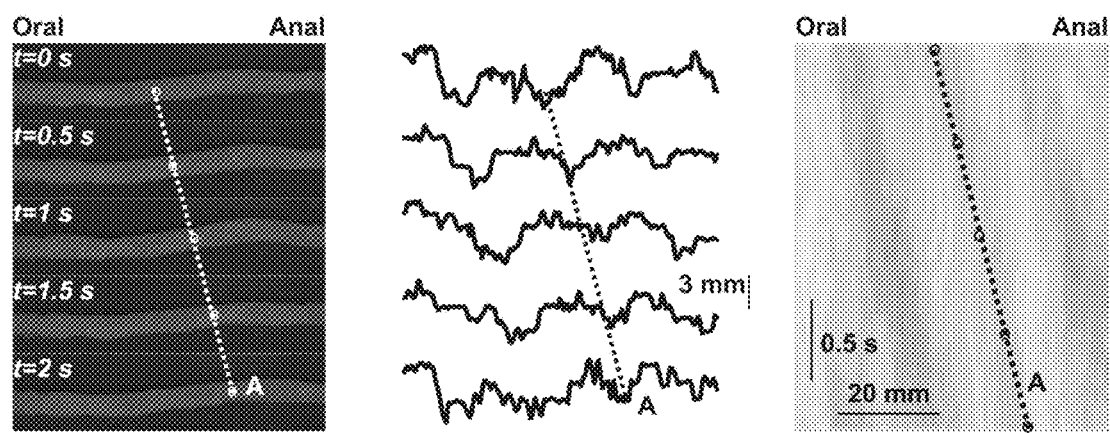
FIG. 3 Picture and data output from motility recordings

Motility parameters were measured directly from the spatiotemporal map using the StMap plugin. In this system we are able to test (using tetrodotoxin neuron silencing) whether contractions depend on the enteric nervous system or are myogenic (driven by rhythmic muscle contractions but neuron independent) Neurally generated, anally propagating, migrating motor complexes MCs generated thick dark bands that slant diagonally from left to right; the propagation velocity (mm $s^{-1}$) is measured from the slope(s) of each band (FIG. 3). For each treatment, slopes of 3-5 successive MCs were averaged to calculate the propagation velocity. MC frequency (mHz) was gauged by counting the number of dark MC bands during a 10 min segment. MC amplitude was measured directly from the baseline diameter (FIG. 2B) or pressure (FIG. 2C) to the next peak with 3 values being averaged for each treatment. The rate of diameter change (cm/s) was calculated from the time taken for the diameter to constrict maximally from baseline (downstroke of MCs in (FIG. 2B).

Agents to be Tested

*Lactobacillus rhamnosus* (JB-1), *Lactobacillus reuteri* (DSM 17938), *Lactobacillus reuteri* ATCC PTA 6475, *Lactobacillus gasseri* 345A (DSM 27123), *Lactobacillus gasseri* 621A (DSM 27126), *Lactobacillus gasseri* T1 and *Lactobacillus gasseri* T2 were all tested in the first step of the methods of the invention.

Cell numbers were determined optically and viability was always checked by ability to grow after plating on growth medium agar plates. Cells from frozen stocks were thawed and centrifuged at 2000 rpm for 15 min, and the pellet was suspended in equal volume of Krebs buffer. Then the suspension was again centrifuged, and the cells were removed and resuspended in Krebs at the original concentration. Just prior to use, bacteria were diluted to working concentrations with fresh Krebs buffer.

Krebs containing bacteria were fed to the intraluminal compartment while ion channel modulating drugs added to the Krebs buffer perfusing the serosal compartment. The time required for the drug solution to flow from the tap to the recording chamber was 30 s. The $IK_{Ca}$ ion channel blocker 1-[(2-chlorophenyl)diphenylmethyl]-1H-pyrazole (TRAM-34) (Tocris Bioscience, Ellisville, Mo., USA) was dissolved with pure dimethyl sulfoxide (DMSO) to make 10-mM stock solutions, and these were diluted in oxygenated Krebs to make working concentrations 30 min before use. The IK$_{Ca}$ channel opener, 5,6-dichloro-1-ethyl-2-benzimidazolinone (DCEBIO) (Tocris) was dissolved in DMSO to make a 10-mM stock solution; the final working concentration in Krebs buffer was 0.1 or 1 µM.

Figures 7A, 7B, 7C:
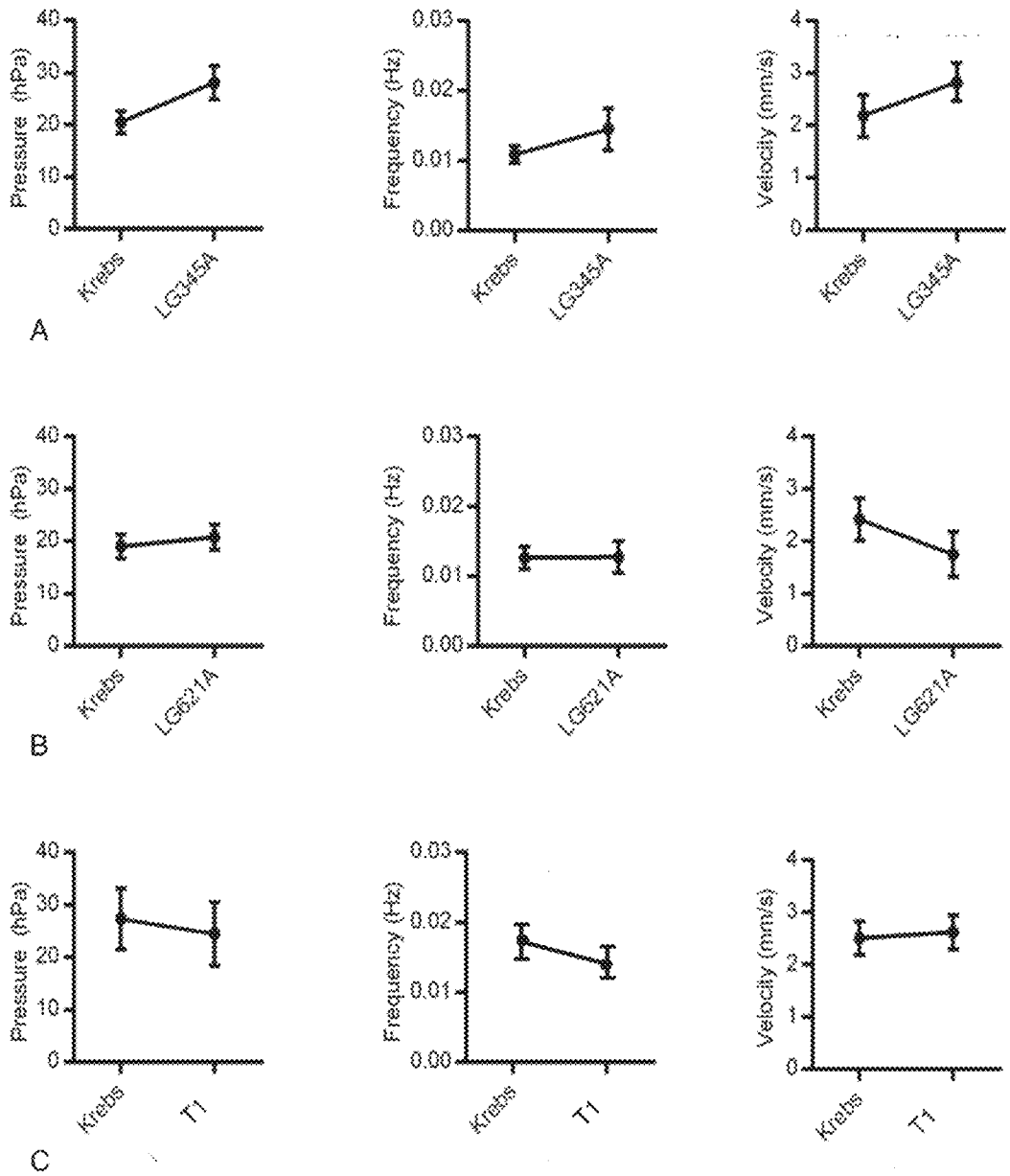
FIG. 7A-7G Graphs showing the results of step a). Agents tested are (FIG. 7A) L. gasseri 345A (DSM 27123), (FIG. 7B) L. gasseri 621A (DSM 27126), (FIG. 7C) L. gasseri T1, (FIG. 7D) L. gasseri T2, (FIG. 7E) L. reuteri ATCC PTA 6475, (FIG. 7F) L. reuteri DSM 17938 and (FIG. 7G) L. rhamnosus (JB-1).
Figures 7D, 7E, 7F, 7G:
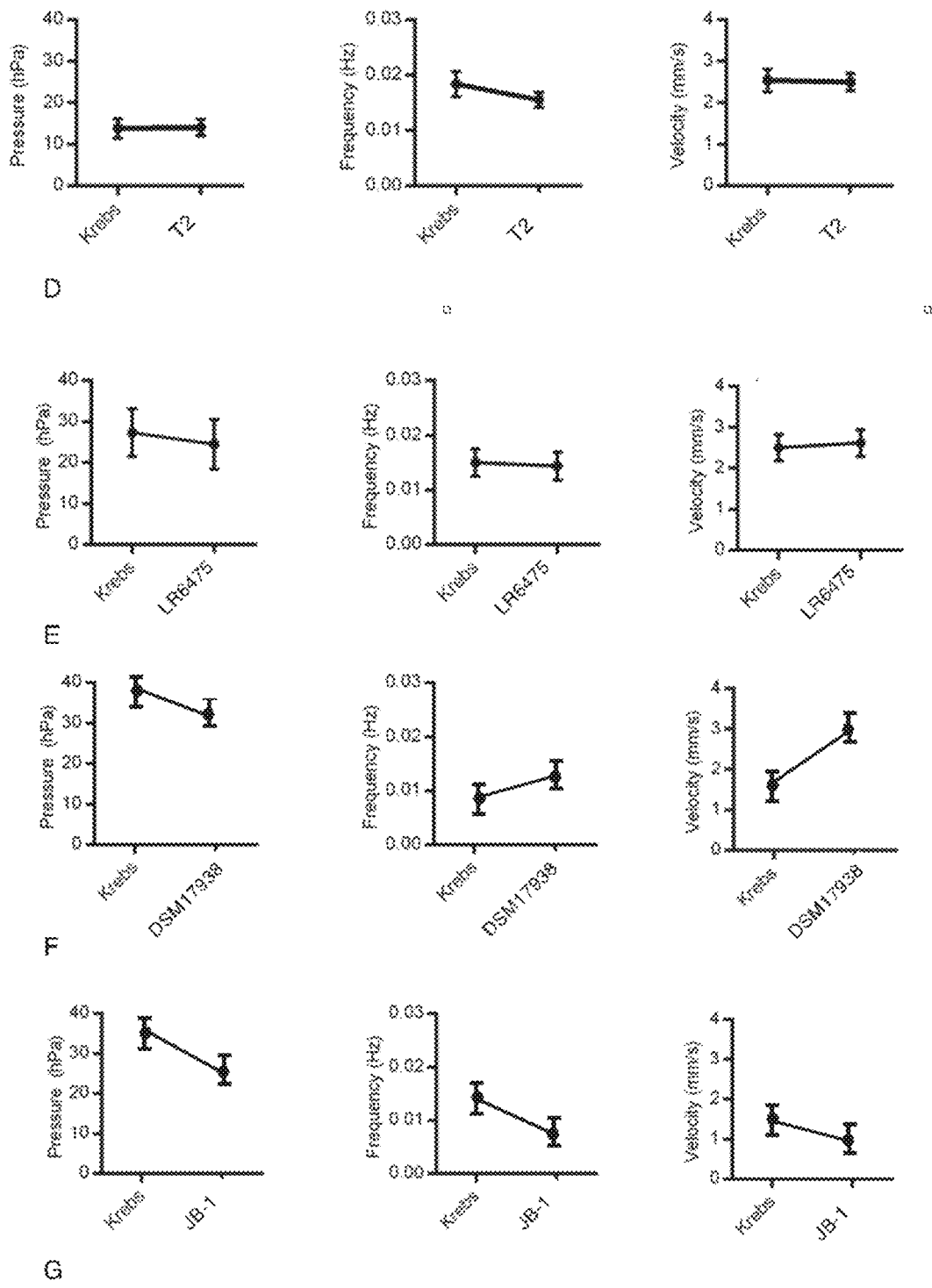

The agents are analyzed according to the presented step 1 above and the results are shown in FIG. 7

Statistics

Statistics were calculated using GraphPad Prism 5.0 (GraphPad Software, San Diego, Calif., USA). Descriptive statistics are given as means±SD, but in concentration-response plots, sampling errors are displayed using SEM; the sample size is denoted by n. The statistically discernible difference for tests of significance was set at P=0.05; all tests were 2-tailed.

Second Step, the Analysis of Nerve Signaling

All procedures adhered to Canadian Council on Animal Care guidelines and were approved by the Animal Research Ethics Board of McMaster University (Permit #08-08-35).

Extracellular Recordings

Figure 4:
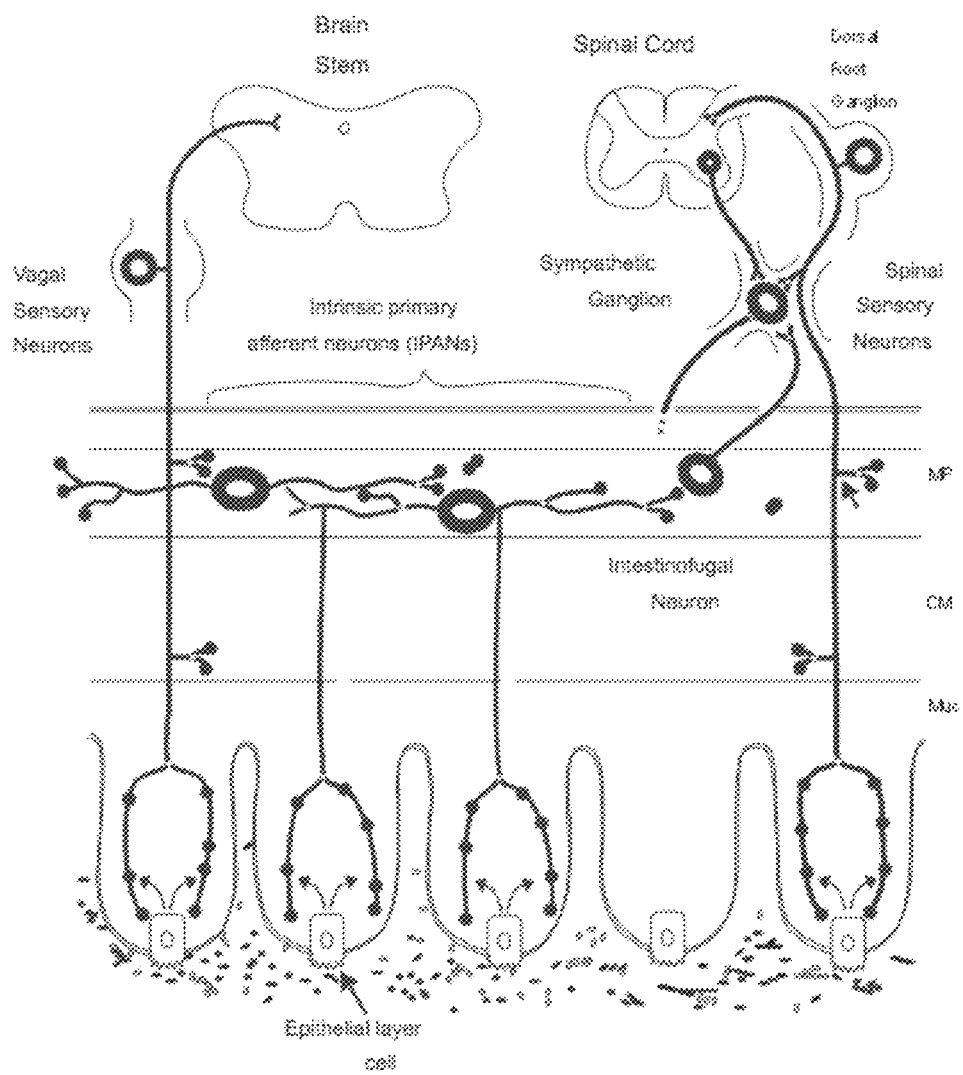
FIG. 4 Mesenteric nerve recording; innervation of the intestine
Figure 5:
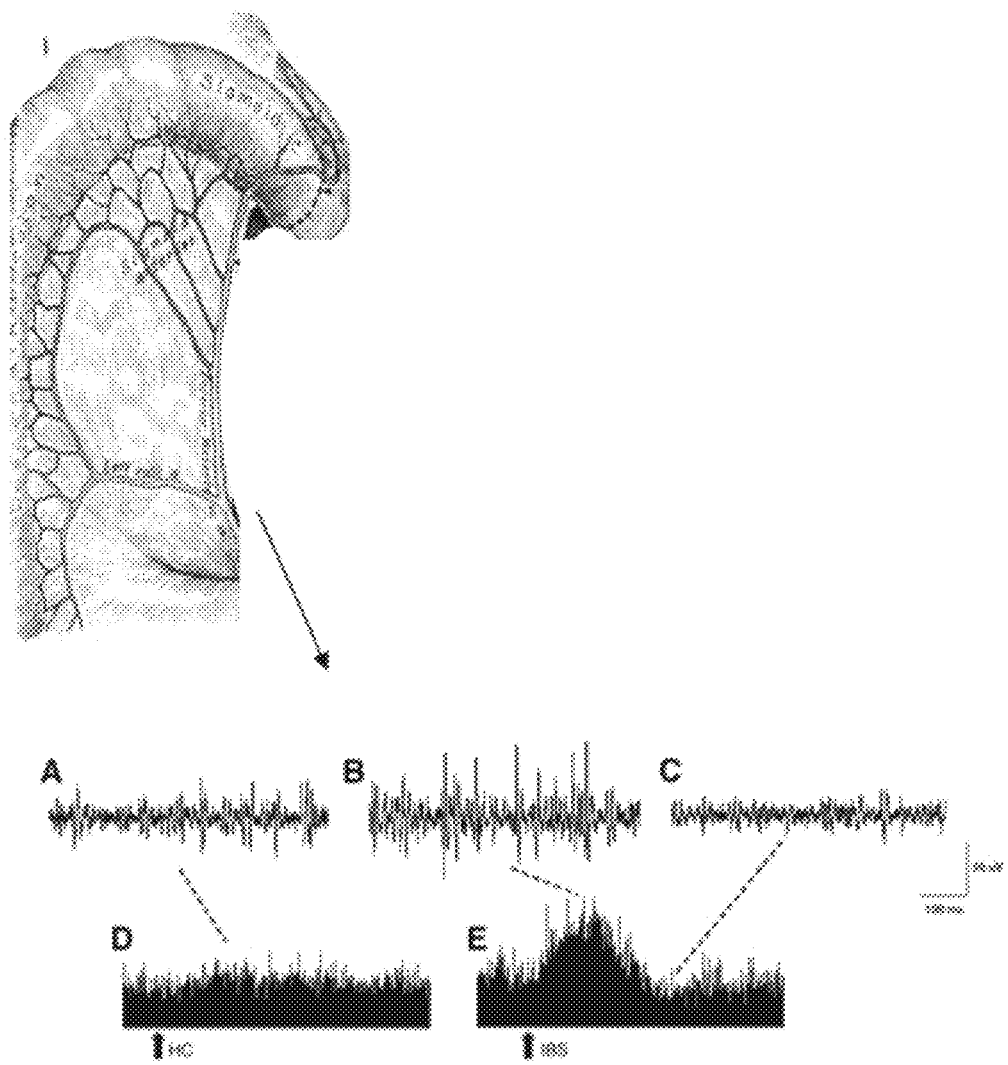
FIG. 5 Extracellular recordings

Adult male Swiss Webster mice (20-30 g) were procured from Charles River Laboratories (Wilmington, Mass., USA). The mice were sacrificed by cervical dislocation. All ensuing procedures were ex vivo. Segments of excised distal jejunum (~2.5 cm) with attached mesenteric tissue were removed from euthanized animals (FIG. 4) and immediately placed in a Sylgard-coated recording Petri dish filled with Krebs buffer of the following composition (mM): 118 NaCl, 4.8 KCl, 25 NaHCO3, 1.0 NaH2PO4, 1.2 MgSO4, 11.1 glucose and 2.5 CaCl2 bubbled with carbogen (95% O2/5% CO2). The oral and anal ends of the gut segment were cannulated with plastic tubing and gently emptied using an attached syringe filled with oxygenated Krebs buffer; then, the segment and mesenteric tissue were pinned out and the mesenteric nerve bundle isolated by careful dissection under a stereo microscope (FIG. 5) as described by Barbara et al (Gastroenterology, Volume 132, Issue 1, Pages 26-37, January 2007). The preparation was transferred to an inverted microscope and the lumen gravity perfused at 0.5-1 ml/min with room temp (~22° C.) oxygenated Krebs and/or additives using several Mariotte bottles. The serosal compartment was separately perfused with prewarmed (34° C.) Krebs solution at 3-5 ml/min. The nerve bundle was gently drawn by suction into a glass pipette attached to a patch clamp electrode holder (CV-7B; Molecular Devices, Sunnyvale, Calif., USA) and extracellular nerve recordings were made using a Multi-Clamp 700B amplifier and Digidata 1440A signal converter (Molecular Devices). Electrical signals were bandpass-filtered at 0.1 to 2 kHz, sampled at 20 kHz and stored on a personal computer running pClamp 10 software (Molecular Devices) for post-hoc analysis.

Vagotomy

For some experiments, a subdiaphragmatic vagotomy was carried out as previously described (van der Kleij H., Am J Physiol Regul Integr Comp Physiol 295:1131-1137, 2008)). Animals were allowed to recover for 10-14 days before harvesting the jejunum and mesenteric tissue for electrophysiological experiments. Sham vagotomy was performed in 3 animals. Post-operatively, the body weight and general health of the mice were measured daily. We found no evidence of significant differences in weight gain 1 week post-surgery in either vagotomized or sham-treated animals. All vagotomized mice were tested for completeness of the procedure by recording after each experiment the responses to the serosal application of cholecystokinin (CCK).

Vagotomy was deemed to have been effective when we found that CCK did not increase mesenteric nerve firing rate.

Integrity of Jejunal Segments

To test the integrity of the jejunal segments with respect to translocation of bacteria across the epithelium during an experiment, we labeled JB-1 with 5-(6)-carboxyfluorescein succinimidyl ester (CFSE), placed these at a concentration of $10^9$/ml Krebs into the lumen and after incubation for 75 min, fixed the tissue in paraformaldehyde, and examined sections for their presence below the epithelium in confocal microscopy (dual-laser microscopy, LSM 510, Carl Zeiss, Germany). JB-1 were washed twice in PBS and suspended in a final concentration of CFSE of 5 µM in PBS supplemented with 5% fetal calf serum and incubated for 25 min at 37° C. The tissues (n=3) were fixed in 4% paraformaldehyde at 4° C. overnight, then washed 3 times in PBS for 10 min each, sectioned at 10 and 30 µm and transverse sections transferred to microscope slides and mounted. These were then reviewed in optical slices by Z-stacking methodology.

Agents to be Tested

*Lactobacillus rhamnosus* (JB-1), *Lactobacillus reuteri* (DSM 17938), *Lactobacillus reuteri* ATCC PTA 6475, *Lactobacillus gasseri* 345A (DSM 27123), *Lactobacillus gasseri* 621A (DSM 27126), *Lactobacillus gasseri* T1 and *Lactobacillus gasseri* T2 were all tested in the second step of the methods of the present invention.

Cell numbers were determined optically, and viability checked by the ability to grow after plating on growth medium agar plates. Live *L. rhamnosus* were grown from frozen (−80° C.) 1 ml aliquots, which consisted of 5×$10^9$ cells in Man-Rogosa Sharpe broth (Difco Laboratories, Sparks, Md., USA). Cells from frozen stocks were thawed and centrifuged at 2000 rpm for 15 min, and the pellet was suspended in equal volume of Krebs buffer. The suspension was again centrifuged, and the cells removed and resuspended in Krebs at the original concentration. Just prior to use, the cells were diluted to working concentrations with Krebs buffer. For some experiments the bacteria were diluted directly to working concentrations after thawing (in broth); the bacteria were always applied into the lumen of the jejunal segment. Cholecystokinin (25-33) sulphated (CCK; AnaSpec, Fremont, Calif.) was dissolved in DMSO to make a 1 mM stock solution. Aliquots were diluted on the day of the experiment to working concentration in Krebs buffer, with a final DMSO concentrations ≤0.0001%.

Off-Line Data Analysis

Figure 8:
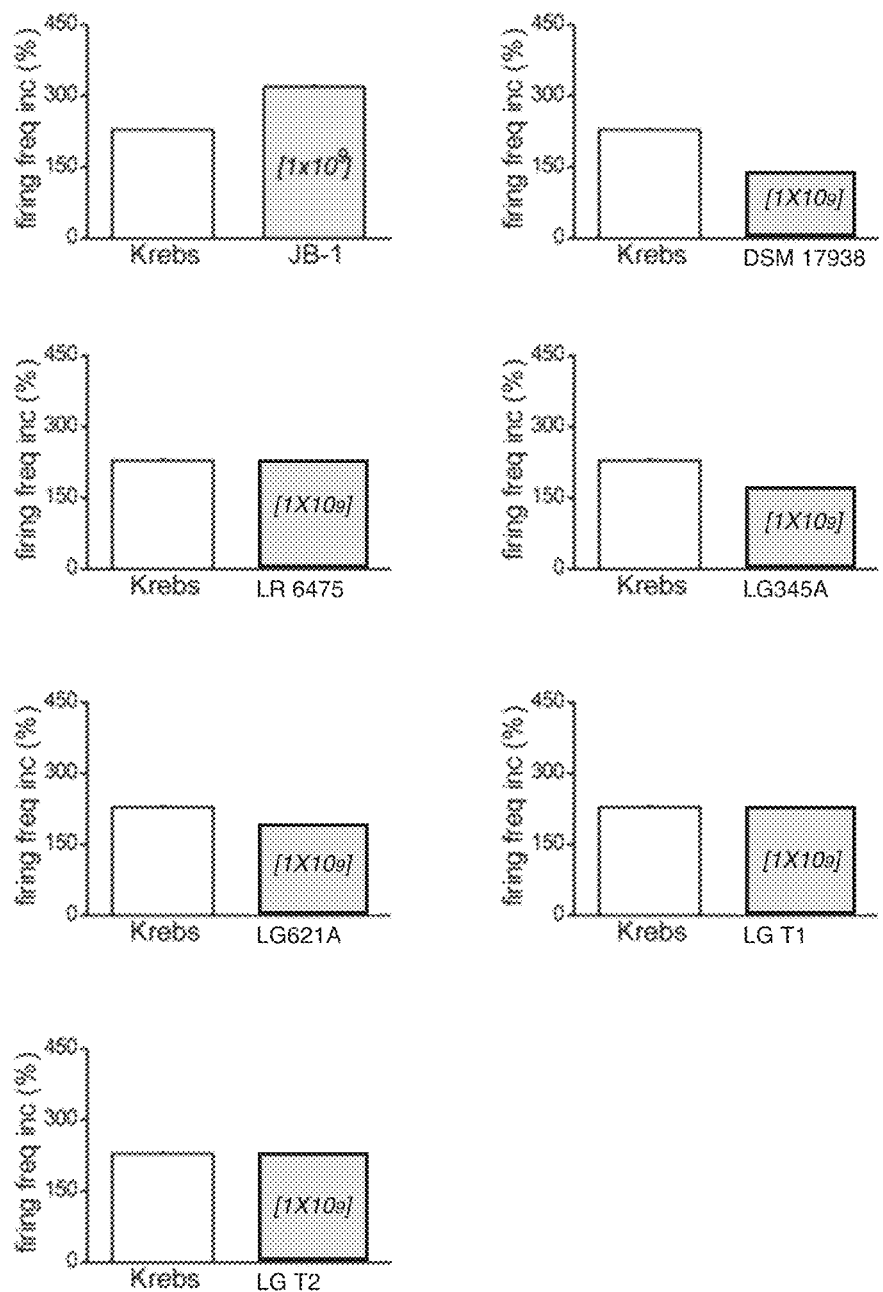
FIG. 8 Graphs showing the results of step b), agents tested are L. rhamnosus (JB-1), L. reuteri DSM 17938, L. reuteri ATCC PTA 6475, L. gasseri 345A (DSM 27123), L. gasseri 621A (DSM 27126), L. gasseri T1 and L. gasseri T2.

Multi- and single-unit spontaneous firing frequencies of mesenteric afferent nerve bundles were measured using Clampfit 10.2 (Molecular Devices). Both methods (multi-unit spike discharge and waveform analysis) of measurement are routinely used to determine changes in the excitability of the mesenteric nerve fibers induced by different treatments. The timing of multi-unit spikes was determined using the peak detection module of Clampfit, and average frequency calculated from spike intervals. Single-unit activity was isolated from the multi-unit activity using the spike shape automatic template detection tool of Clampfit (computerized waveform analysis). After template detection, discrimination was always checked by visual inspection and visually non-spike shapes events were discarded (<0.2%). The results are presented in FIG. 8.

Statistics

Data are expressed as means±SEM with n referring to the total number of the jejunal segments recorded; the maximum number of segments recorded from the same animal was two. The Wilcoxon test was used for paired data comparisons and Friedman test with Dunn's post hoc test for repeated measures analysis of variance were performed using Prism software 5.0 (GraphPad Software, Inc., San Diego, Calif.). Because large variations in spontaneous activity may occur between one preparation and another in multi-unit neural activity, all comparisons were paired with before and after treatment recordings made where each nerve bundle served as its own control. Differences were considered significant if P≤0.05.

EXAMPLE 3

A. Selection of Optimal Probiotic Bacterial Agents to Help Treat Motility Disorders (e.g. Constipation in the Elderly) Using the Defined Steps of the Present Invention;

*L. rhamnosus* (JB-1), *Lactobacillus reuteri* (DSM 17938), *Lactobacillus reuteri* ATCC PTA 6475, *Lactobacillus gasseri* 345A (DSM 27123), *Lactobacillus gasseri* 621 IA (DSM 27126), *Lactobacillus gasseri* T1 and *Lactobacillus gasseri* T2 is analyzed according to example 2. The results are summarized in table 1.

TABLE 1

| Agent | | Motility | | Pain signaling |
|---|---|---|---|---|
| | | Jejunum | Colon | |
| JB-1 | MMC frequency | ↓ | ↓ | ↑ |
| | MMC velocity | ↑ | ↓ | |
| | PPr | ↓ | ↓ | |
| DSM 17938 | MMC frequency | ↓ | ↑ | ↓ |
| | MMC velocity | ↓ | ↑ | |
| | PPr | ○ | ○ | |
| ATCC PTA 6475 | MMC frequency | — | ○ | ○ |
| | MMC velocity | — | ○ | |
| | PPr | — | ○ | |
| LG345A | MMC frequency | — | ↑ | ↓ |
| | MMC velocity | — | ↑ | |
| | PPr | — | ↑ | |
| LG621A | MMC frequency | — | ○ | ↓ |
| | MMC velocity | — | ↓ | |
| | PPr | — | ○ | |
| T1 | MMC frequency | — | ○ | ○ |
| | MMC velocity | — | ○ | |
| | PPr | — | ↓ | |
| T2 | MMC frequency | — | ↓ | ○ |
| | MMC velocity | — | ○ | |
| | PPr | — | ○ | |

Table 1

*L. reuteri* DSM 17938 and *L. gasseri* 345A increase the MMC velocity in the colon and also increases at least one of the parameters PPr or MMC frequency in the colon (*L. reuteri* DSM 17938 increases the MMC frequency and *L. gasseri* 345A increases the PPr). Both these strains decrease the frequency of spontaneous firing of mesenteric afferent nerve bundles. Therefore these strains are selected for treatment of colic, e.g. infantile colic, since these strains increase the speed of MC propagation flow and at the same time decrease the frequency of firing of mesenteric afferent nerve bundles.

The increase in MMC velocity and the decrease of the frequency of spontaneous firing of mesenteric afferent nerve bundles caused by *L. retueri* DSM 17938 and *L. gasseri* 345A makes them suitable for treatment of constipation, especially in pregnant women where a reduction is wanted, or in the elderly.

*L. rhamnosus* JB-1 and *L. gasseri* 621A decrease the MMC velocity. *L. gasseri* 621A also decreases the frequency of the firing of mesenteric afferent nerve bundles and can therefore be used for treating disorders involving rapid passage transit, for example IBS. *L. rhamnosus* JB-1 has no effect on the frequency of firing of mesenteric afferent nerve bundles and is therefore not applicable for treatment of motility disorders.

*L. reuteri* ATCC PTA 6475, *L. gasseri* T1 and *L. gasseri* T2 does not show any effect on neither MMC velocity nor the spontaneous frequency of firing of mesenteric afferent nerve bundles and is therefore not recommended for use in motility disorders.

DEPOSIT INFORMATION

A deposit of the proprietary bacterial strains *Lactobacillus gasseri* 345A and *Lactobacillus gasseri* 621A has been made with the Leibniz Institute DSMZ (DSMZ)—German Collection of Microorganisms and Cell Cultures, Inhoffenstr. 7B, D-38124 Braunschweig, Germany. The date of deposit for *Lactobacillus gasseri* 345A and *Lactobacillus gasseri* 621A was Apr. 18, 2013. Upon issuance of a patent, all restrictions upon the deposits will be removed, and the deposits are intended to meet all of the requirements of 37 C.F.R. §1.801-1.809. The DSMZ has issued accession number DSM 27123 for *Lactobacillus gasseri* 345A and accession number DSM 27126 for *Lactobacillus gasseri* 621A. These deposits will be maintained in the depository for a period of 30 years, or 5 years after the last request, or for the effective life of the patent, whichever is longer, and will be replaced as necessary during that period. Applicants do not waive any infringement of their rights granted under this patent or under the Plant Variety Protection Act (7 U.S.C. 2321 et seq.).

The invention claimed is:

1. A bacterial strain that increases migrating motor complex (MMC) frequency, MMC velocity and intraluminal peak pressure, and decreases mesenteric afferent nerve firing, wherein the bacterial strain is *Lactobacillus gasseri* 345A (LG345A) having been deposited under DSMZ Accession No. DSM 27123.

2. A bacterial strain that decreases MMC velocity and decreases mesenteric afferent nerve firing, wherein the bacterial strain is *Lactobacillus gasseri* 621A (LG621A) having been deposited under DSMZ Accession No. DSM-27126.

3. The bacterial strain of claim 1, wherein the bacterial strain decreases pain signaling when administered to a subject.

4. The bacterial strain of claim 1, wherein the bacterial strain increases gastrointestinal motility when administered to a subject, thereby decreasing the transit time of material through the intestine of said subject.

5. The bacterial strain of claim 2, wherein the bacterial strain decreases pain signaling when administered to a subject.

6. The bacterial strain of claim 2, wherein the bacterial strain decreases gastrointestinal motility when administered to a subject, thereby increasing the transit time of material through the intestine of said subject.

7. The bacterial strain of claim 4, wherein decreasing the transit time of material through the intestine of said subject treats or reduces the risk of developing constipation or colic in said subject.

8. The bacterial strain of claim 6, wherein increasing the transit time of material through the intestine of said subject treats or reduces the risk of developing irritable bowel syndrome in said subject.

9. A composition comprising the bacterial strain of claim 1 and a pharmaceutically acceptable carrier, diluent or excipient.

10. A composition comprising the bacterial strain of claim 1 and a foodstuff or food supplement.

11. A composition comprising the bacterial strain *Lactobacillus gasseri* 345A and a further therapeutic or nutritional agent.

12. A composition comprising the bacterial strain of claim 2 and a pharmaceutically acceptable carrier, diluent or excipient.

13. A composition comprising the bacterial strain of claim 2 and a foodstuff or food supplement.

14. A composition comprising the bacterial strain *Lactobacillus gasseri* 621A and a further therapeutic or nutritional agent.

* * * * *

UNITED STATES PATENT AND TRADEMARK OFFICE
CERTIFICATE OF CORRECTION

| | | |
|---|---|---|
| PATENT NO. | : 9,816,150 B2 | Page 1 of 1 |
| APPLICATION NO. | : 15/389577 | |
| DATED | : November 14, 2017 | |
| INVENTOR(S) | : Connolly et al. | |

It is certified that error appears in the above-identified patent and that said Letters Patent is hereby corrected as shown below:

In the Specification

Column 15, Line 36: Please correct "Oz" to read -- $O_2$ --

Signed and Sealed this
Third Day of July, 2018

Andrei Iancu
*Director of the United States Patent and Trademark Office*